United States Patent
Parton et al.

(10) Patent No.: US 9,056,829 B2
(45) Date of Patent: Jun. 16, 2015

(54) PROCESS FOR THE ALKOXYCARBONYLATION OF FUNCTIONALIZED ALKENES

(75) Inventors: Rudy Francois Maria Jozef Parton, AA Echt (NL); Michèle Catherine Christianne Janssen, AA Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/240,816

(22) PCT Filed: Aug. 31, 2012

(86) PCT No.: PCT/EP2012/066970
§ 371 (c)(1),
(2), (4) Date: Mar. 21, 2014

(87) PCT Pub. No.: WO2013/030344
PCT Pub. Date: Mar. 7, 2013

(65) Prior Publication Data
US 2014/0206893 A1    Jul. 24, 2014

Related U.S. Application Data

(60) Provisional application No. 61/530,141, filed on Sep. 1, 2011.

(30) Foreign Application Priority Data

Sep. 1, 2011 (EP) .................... 11179766

(51) Int. Cl.
| | | |
|---|---|---|
| *C07C 67/62* | (2006.01) | |
| *C07C 69/40* | (2006.01) | |
| *C07C 69/003* | (2006.01) | |
| *B01J 31/24* | (2006.01) | |

(52) U.S. Cl.
CPC ............. *C07C 67/62* (2013.01); *B01J 31/2409* (2013.01); *B01J 2231/321* (2013.01); *B01J 2531/824* (2013.01); *C07C 69/003* (2013.01); *C07C 69/40* (2013.01)

(58) Field of Classification Search
CPC ....................................................... C07C 67/62
USPC ........................................................ 560/204
See application file for complete search history.

(56) References Cited

FOREIGN PATENT DOCUMENTS

| | | | |
|---|---|---|---|
| CN | 1127245 A | | 7/1996 |
| CN | 1127254 A | * | 7/1996 |
| EP | 0274795 A2 | | 7/1988 |
| WO | 0110551 A1 | | 2/2001 |

OTHER PUBLICATIONS

International Search Report corresponding to PCT/EP2012/066970 mailed Oct. 18, 2012.

\* cited by examiner

*Primary Examiner* — Yong Chu
(74) *Attorney, Agent, or Firm* — Miles & Stockbridge PC

(57) ABSTRACT

This invention relates to a process for the alkoxycarbonylation of carboxylic acid functionalized alkenes or esters thereof, said process comprising: (a) reacting (i) a carboxylic acid functionalized alkene or ester thereof; (ii) a catalyst system comprising a source of Pd and a ligand, (iii) a source of anions derived from an acid with a $pK_a<3$, (iv) carbon monoxide, and (v) a hydroxylgroup comprising compound, under conditions wherein an ester carbonylation product is produced, whereby the process is carried out in the initial presence of an ester carbonylation product. The presence of the ester carbonylation product results in stabilization of the catalyst system and prevents the formation of Pd black.

12 Claims, 1 Drawing Sheet

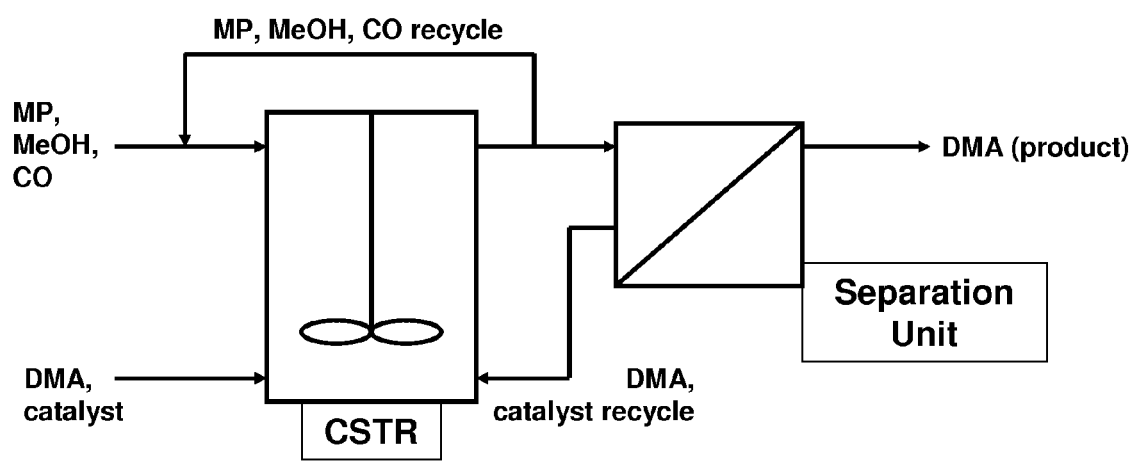

US 9,056,829 B2

PROCESS FOR THE ALKOXYCARBONYLATION OF FUNCTIONALIZED ALKENES

CROSS REFERENCE TO RELATED APPLICATIONS

This application is a §371 National Stage Application of PCT/EP2012/066970, filed Aug. 31, 2012, which claims priority to European Application No. 11179766.8, filed Sep. 1, 2011, and to U.S. Provisional Application No. 61/530,141, filed Sep. 1, 2011.

BACKGROUND OF THE INVENTION

1. Field of the Invention

The present invention relates to a process for the carbonylation of optionally functionalized alkenes.

2. Description of Related Art

WO01/10551 discloses a carbonylation reaction using a Pd catalyst system. A problem associated with such carbonylation reactions is that the catalyst system tends to inactivate over time. Especially in processes wherein the catalyst is used repetitively or continuously, inactivation of the Pd catalyst system may form a problem. The problem is understood to reside in the reduction of the ionic Pd to metallic Pd. Such process is also referred to as the formation of Pd black. To compensate for the loss in activity additional Pd catalyst must be added. Pd black may adhere to the wall of the reactor.

In order to overcome the inactivation or Pd black formation WO0110551 proposes to carry out the carbonylation process in the presence of polymeric dispersants. A disadvantage of the use of polymeric stabilizers is that they are not required for the chemical conversion per se and their use means extra cost. Another disadvantage of using a polymeric dispersant is that it must be separated from the carbonylation product.

SUMMARY

The invention discloses herewith a process for the carbonylation of optionally functionalized alkenes, said process comprising:
(a) reacting (i) an optionally functionalized alkene; (ii) a catalyst system comprising a source of Pd and a ligand, (iii) a source of anions derived from an acid with a $pKa < 3$, (iv) carbon monoxide, and (v) a hydroxylgroup comprising compound, under conditions wherein an alkene carbonylation product is produced, whereby the process is carried out in the presence of alkene carbonylation product.

BRIEF DESCRIPTION OF THE DRAWINGS

FIG. 1 depicts an embodiment as described herein.

DETAILED DESCRIPTION OF PREFERRED EMBODIMENT

Within the context of the invention, "alkene carbonylation product" is understood to include optionally functionalized alkene carbonylation products, such as ester carbonylation products.

The process of the invention may be a continuous process. Any continuous reactor type is suitable. Examples of suitable reactor types are continuous stirred-tank reactor (CSTR) and plugflow. In a CSTR reactor once steady state is reached the concentration of components in the reactor does not change anymore: reactants are withdrawn and substrate is added such that their concentrations remain the same in the reactor. In a plugflow reactor, for example a packed bed reactor (PBR) the conversion depends on the residence time, which in turn is a function of its position in the reactor. Plugflow reactors are often selected when the product is susceptible to a further reaction. If the alkene carbonylation product is reactive, a PFR reactor is preferred. If the alkene carbonylation product is not very reactive, for example in the case of dimethyl adipate, a CSTR reactor, or a series of CSTR reactors, is preferred.

In a continuous process the concentration of the catalyst system, the alkene, and the alkene carbonylation product remains unchanged throughout the process. It is only during the start-up phase of continuous processes known in the art that no alkene carbonylation product is present, since it has yet to be produced. In the process of the invention this start-up phase is critical in that the carbonylation product should be initially present.

The steady-state amount of the carbonylation product in the continuous process may depend on the type of reactor and is preferably selected such that the catalyst system is stabilized and the yield is satisfactory. At the start of a continuous process, i.e. before the process is in the continuous phase, no alkene carbonylation product has yet been formed. This situation may for instance occur when a continuous process is started for the first time, or for example after a process is re-started, e.g. after a maintenance stop. During a start-up or restart phase the catalyst system cannot be stabilized by the alkene carbonylation product because there is no alkene carbonylation product yet. Therefore, it is essential that the alkene carbonylation product is initially present in the continuous process. Once the process is in the continuous, i.e. steady-state phase, adding of alkene carbonylation product as stabiliser may no longer be required. Simply be adjusting the concentration of alkene carbonylation product in the continuous phase the skilled person may arrive at a suitable a desired stabilization of the catalyst system without the need to add any stabilizer. In contrast, when using other stabilizers such as polymeric dispersants these may have to be added continuously as they may be removed from the process during recovering of the alkene carbonylation product.

The process of the invention may be a repetitive batch process, wherein said repetitive batch process preferably further comprises
(b) recovering the catalyst system from the alkene carbonylation product in the presence of the alkene carbonylation product; and
(c) repeating step (a) wherein at least part of the catalyst system in step (a) is the recovered catalyst system obtained in step (b).

The repetitive batch process according to the invention preferably comprises two or more consecutive processes. Preferably the repetitive batch process according to the invention comprises three or more consecutive processes, more preferably four or more consecutive processes, five or more consecutive processes, six or more consecutive processes, seven or more consecutive processes, eight or more consecutive processes.

A repetitive batch process including steps (b) and (c) has the advantage that in the recovery step (b) no very stringent separation is required. The inventors have realized that the stabilizing effect of the alkene carbonylation product on the catalyst system of the invention may be applied in a repetitive batch process by recovering the catalyst system in the presence of said alkene carbonylation product. Normally, in a process wherein a catalyst stabilizer is used the skilled person when recovering said catalyst will try to retain as much stabilizer as possible. However, in practice the efficiency of the recovery of the catalyst system from the reaction product is never 100% and some catalyst stabilizer will be lost. This may for example be the case when reaction involves the production of volatile compounds and where these compounds are removed by distillation. In such cases a catalyst stabiliser may also be removed by evaporation. In contrast, the recovery in step (b) of the process of the invention does not have to be very efficient; in fact, the presence of alkene carbonylation product with the catalyst system is advantageous. As a consequence, the recovery step (b) may be easier and/or less expensive. The recovery may also advantageously be done using simple and inexpensive separation technology and/or with less-trained operators. Another advantage is that by using the recovered catalyst system obtained in step (b) in the carbonylation reaction in step (a), no extra addition of alkene carbonylation product is required, which may be less cost and time consuming. It would not be obvious to recover the catalyst system in the presence of alkene carbonylation product. For example, in WO/0168583 the carbonylation reaction is done in excess methanol so it would be logical for the skilled person to recover the catalyst system in the presence of methanol. Moreover, WO/0168583 is silent on recovery of the catalyst system.

The ratio of the alkene carbonylation product:Pd is at least 500:1 based on dry weight. Preferably, the ratio of the alkene carbonylation product:Pd in the process is at least 900:1; more preferably at least 1750:1, all based on dry weight.

It will be understood that "recovering the catalyst system from the alkene carbonylation product" in step (b) does not necessarily mean that the catalyst system is completely separated from the alkene carbonylation product. Complete recovery would mean that catalyst system would be devoid of the alkene carbonylation product, and this may result in inactivation of the catalyst system. Although it is an aim of step (b) to recover the catalyst system from the alkene carbonylation product, it is essential that the catalyst system always comprises at least some alkene carbonylation product.

The ratio of the carbonylation product:Pd in the recovering of the catalyst system in step (b) is at least 500:1 based on dry weight.

At least 10% (w/w) of the catalyst system in step (a) may be the recovered catalyst system obtained in step (b). More preferably at least 20% w/w, at least 30% (w/w), more preferably at least 40% (w/w), 50% (w/w), even more preferably at least 60% (w/w), at least 70% (w/w), even more preferably at least 80% (w/w), 90% (w/w) of the catalyst system in step (a) may be the recovered catalyst system obtained in step (b). Most preferably all catalyst system in step (a) is the recovered catalyst system obtained in step (b).

The ligand in the process of the invention may be a bidentate diphosphine ligand of formula I:

wherein $P_1$ and $P_2$ represent phosphorus atoms; $R_1$, $R_2$, $R_3$ and $R_4$ independently represent the same or different optionally substituted organic groups containing a tertiary carbon atom through which the group is linked to the phosphorus atom and optionally comprising one or more heteroatoms; and wherein R represents a bridging group spanning $P_1$ and $P_2$ and comprising one or more carbon atoms and optionally one or more heteroatoms.

The bidentate diphosphine ligand of formula I may comprise $R_5$—X—$R_6$ wherein $R_5$ and $R_6$ independently represent optionally substituted alkylene groups and X represents an optionally substituted aromatic group. In other words, R may represent $R_5$—X—$R_6$.

Thus, the ligand may be a bidentate diphosphine ligand of formula II:

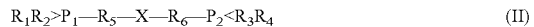

wherein $P_1$, $P_2$, $R_1$, $R_2$, $R_3$, $R_4$, $R_5$, $R_6$, and X are defined as above.

Preferably the optionally substituted alkylene group which $R_5$ or $R_6$ represents, or which $R_5$ and $R_6$ represent, is a lower alkylene group. In the context of the invention "a lower alkylene group" is defined as an alkylene group having 4 C atoms or less, more preferably having 3 C atoms or less, even more preferably having 2 C atoms or less, most preferably the lower alkylgroup is methylene. The number of C atoms in $R_5$ and $R_6$ are not necessarily the same. For example, $R_5$ may have 2 C atoms whereas $R_6$ may have one C atom, or vice versa. Preferably, the alkylene group which $R_5$ and/or $R_6$ represent are non-substituted.

$R_1$, $R_2$, $R_3$, and $R_4$ in the bidentate diphosphine of formula I or formula II may be tert-butyl, $R_3$ and $R_4$ may be methylene, and/or R or X may be ortho-phenylene or ortho-napthalene. $R_5$ and/or $R_6$ are preferably methylene. A suitable ligand is α,α'-bis(di-tert-butylphosphino)xylene.

The length of the bridge formed by R spanning $P_1$ and $P_2$ in the bidentate diphosphine of formula I or of X spanning $R_5$ and $R_6$ in the bidentate diphosphine of formula II may be between 1 and 20 atoms, more preferably between 2-10 atoms, even more preferably between 2 and 6 atoms.

WO01/68583 describes a process for the carbonylation of ethylenically unsaturated compounds using a catalyst system comprising Pd and a bidentate biphosphine ligand. WO01/68583 suggests that the carbonylation reaction can be done in the presence of the ester carbonylation product (e.g. an alkene carbonylation product) as a solvent. The aim of WO/0168583 is to increase the selectivity with respect to linear carbonylation products. The ester carbonylation product is one of a long list of suitable aprotic solvents that can be used in order to increase the selectivity with respect to linear carbonylation product. However, WO/0168583 is silent with respect to continuous or repetitive batch processes, and all examples of WO/0168583 refer to single batch reactions. Moreover, WO/0168583 is silent with respect to a possible stabilization effect of the Pd catalyst system by the presence of ester carbonylation product.

The hydroxylgroup comprising compound may be an alkanol, preferably methanol.

The process of the invention is optionally performed in the presence of an additional solvent, preferably an aprotic solvent. Suitable solvents include ketones, such as for example methylbutylketone; ethers, such as for example anisole (methyl phenyl ether), 2,5,8-trioxanonane (diglyme), diethylether, tetrahydrofuran, 2-methyl-tetrahydrofuran, diphenylether, diisopropylether and the dimethylether of di-ethyleneglycol; esters, such as for example ethyl acetate, methyl acetate, dimethyl adipate and butyrolactone; amides, such as for example dimethylacetamide and N-methylpyrrolidone; and sulfoxides and sulphones, such as for example dimethylsulphoxide, di-isopropylsulphone, sulfolane (tetrahydrothiophene-2,2-dioxide) 2-methylsulfolane and 2-methyl-4-ethylsulfolane. Very suitable are aprotic solvents having a dielectric constant that is below a value of 50, more preferably in the range of 3 to 8, at 298.15 K and 1 bar.

If the hydroxyl group containing compound is an alkanol, a preferred aprotic solvent is the ester carbonylation product of the alkene, carbon monoxide and the alkanol.

The source of anions derived from acid having a pKa below 3.0 (measured in aqueous solution at 18° C.) preferably is a non-coordinating anion. Hereby is meant that little or no covalent interaction takes place between the palladium and the anion.

Examples of suitable anions include anions of phosphoric acid, sulphuric acid, sulphonic acids and halogenated carboxylic acids such as trifluoroacetic acid.

Sulphonic acids are in particular preferred, for example trifluoromethanesulphonic acid, p-toluenesulphonic acid and 2,4,6-trimethylbenzene sulphonic acid, 2-hydroxypropane-2-sulphonic acid, tert-butyl sulphonic acid, methyl sulphonic acid. The acid can also be an ion exchange resin containing sulphonic acid groups.

An especially preferred source of anions derived from an acid having a pKa below 3.0 is methylsulphonic acid, tert-butyl sulphonic acid and/or 2,4,6-trimethylbenzenesulphonic acid.

Suitable sources of Pd in the process of the invention include its salts, such as for example the salts of palladium and halide acids, nitric acid, sulphuric acid or sulphonic acids; palladium complexes, e.g. with carbon monoxide, dienes, such as dibenyzlideneacetone (dba) or acetylacetonate, palladium nanoparticles or palladium combined with a solid carrier material such as carbon, silica or an ion exchanger. Preferably, a salt of palladium and a carboxylic acid is used, suitably a carboxylic acid with up to 12 carbon atoms, such as salts of acetic acid, proprionic acid, butanoic acid or 2-ethyl-hexanoic acid, or salts of substituted carboxylic acids such as trichloroacetic acid and trifluoroacetic acid. A very suitable source is palladium (II) acetate.

The source of Pd may be selected from the group consisting of palladium halide, palladium carboxylate or Pd2(dba)3.

The alkene may be ethene. The product of the methoxycarbonylation of ethene, methyl proprionate, can be further reacted with formaldehyde to form methyl methacrylate. The present invention can lower the cost of an already existing process for the production of methyl methacrylate.

The carbonylation process of the invention may comprise alkoxycarbonylation, preferably methoxycarbonylation.

The alkene in the process of the invention is optionally functionalized. The functionalization may include hydroxyl, amine or amide, and carboxylic acid or esters thereof. Preferred functionalized alkenes are carboxylic acid functionalized alkenes. Preferred alkene carbonylation products are ester carbonylation products.

The alkene carbonylation product preferably has 4-20 C atoms, more preferably 5-8 C atoms, even more preferably 6 C atoms.

Suitable carboxylic acid functionalized alkenes are pentenoates or esters thereof, preferably pentenoate methyl esters. Alkoxycarbonylation of pentenoic acid or pentenoate esters may result in the production of adipic acid esters such as monoesters (adipic acid monomethyl ester) or diesters (adipic acid dimethyl ester), which may be used as an important intermediate in the production of adipic acid (1,6-hexanedioic acid), which itself is an important precursor for inter alia the production of polyamides such as polyamide-6,6 or polyamide-4,6. Further, esters of adipic acid may be used in plasticisers, lubricants, solvent and in a variety of polyurethane resins. Other uses of adipic acid are as food acidulants, applications in adhesives, insecticides, tanning and dyeing. The ester carbonylation product is understood to also include higher esters, e.g. tri, four, five, and polyesters.

In step (a) of the process of the invention the actual carbonylation reaction takes place.

The process of the invention is carried out in the initial presence of alkene carbonylation product. The inventors have surprisingly found out that the initial presence of alkene carbonylation product in the process of the invention may result in stabilisation of said catalyst system. This is all the more surprising since the reaction involves the production of alkene carbonylation product. Nevertheless, it appears that the alkene carbonylation product which is formed in the course of the reaction in step (a) by itself may not stabilise the catalyst system to the same extent as does the initial presence of alkene carbonylation product. At the start of a carbonylation process no or hardly any alkene carbonylation product is present. Therefore, in order to carry out the process of the invention, whether it is a repetitive batch or a continuous process, or any other type of process, the alkene carbonylation product must be added to the reaction medium in step (a) at least once. It would not be obvious to add the reaction product to a chemical conversion reaction, particularly on industrial scale. On the contrary, the reaction product is normally removed from the reaction as efficiently as possible in order to try to sell as much product as possible. Using the process of the invention may result in less formation of Pd black and/or in less inactivation of the catalyst system as compared to a repetitive or continuous carbonylation process which is carried out in the absence of initial carbonylation product. Formation of Pd black is an indication of inactivation of the catalyst.

The process of the invention is particularly advantageous in that no additional stabilizer needs to be added because the stabilizer is the alkene carbonylation product itself.

The alkene carbonylation product which is initially present in the process is not necessarily the alkene carbonylation product which is formed in the process of the invention.

The alkene carbonylation product which is initially present in the process may be the same as the alkene carbonylation product which is formed in the process of the invention. By way of example, if the process of the invention involves methoxycarbonylation of methylpentenoate using methanol and CO resulting in the production of adipic acid methylester, such a process may be carried in the initial presence of adipic acid methylester.

The alkene carbonylation product which is initially present in the process may be a different alkene carbonylation product as compared to the alkene carbonylation product which is formed in the process of the invention. By way of example, if the process of the invention involves methoxycarbonylation of ethene using methanol and CO resulting in the production of methylproprionate, such a process may be carried in the initial presence of adipic acid methylester. Alternatively, if the process of the invention involves methoxycarbonylation of methylpentenoate using methanol and CO resulting in the production of adipic acid methylester, such a process may be carried in the initial presence of methylproprionate.

The alkene carbonylation product which is initially present in the process may comprise at least part of the alkene carbonylation product which is formed in the process of the invention. Using an initial alkene carbonylation product which comprises, or which is the same as the alkene carbonylation product which is formed in the process of the invention may be advantageous in that no additional stabilizer may have to be added. Using an initial alkene carbonylation product which is different from the alkene carbonylation product which is formed in the process of the invention may be advantageous in that such initial alkene carbonylation product may not inhibit the reaction, or to a lesser extent.

In an embodiment, alkene carbonylation product is added to the process only once, for example during the start-up of the process, when no alkene carbonylation product has yet been formed. As the process proceeds alkene carbonylation product is formed which may stabilize the catalyst system.

The initial alkene carbonylation product in the process may comprise at least 10% w/w of the alkene carbonylation product which is formed in the process of the invention, more preferably at least 20% w/w, at least 30% w/w, more preferably at least 40% w/w, at least 50% w/w, even more preferably at least 60% w/w, at least 70% w/w, even more preferably at least 80% w/w, at least 90% w/w. Most preferably the initial alkene carbonylation product is the alkene carbonylation product which is formed in the process of the invention.

The process may comprise the step of adding an alkene carbonylation product. Adding an alkene carbonylation product to the process may ensure the initial presence of alkene carbonylation product.

The alkene carbonylation product may be added to the carbonylation reaction in step (a) in any way. The alkene carbonylation product may be added together with the alkene. The alkene carbonylation product may also be added to the carbonylation reaction in step (a) together with the catalyst system. It is important to not add the carbonylation product after adding the catalyst system since in this case inactivation of the catalyst system may take place. The alkene carbonylation product may be added to the process prior to adding the catalyst system.

Therefore the invention provides a process for the alkoxycarbonylation of carboxylic acid functionalized alkenes or esters thereof, said process comprising:
 adding to a reaction medium an alkene carbonylation product;
 subsequently adding to said reaction medium, in no particular order, an optionally functionalized alkene; a catalyst system comprising a source of Pd and a ligand, a source of anions derived from an acid with a pKa<3, carbon monoxide, and a hydroxylgroup comprising compound; and
 subjecting said components under conditions wherein an alkene carbonylation product is produced.

The invention further provides the use of an ester carbonylation product to stabilise a catalyst system comprising a source of Pd and a ligand in a process for the carbonylation of optionally functionalized alkenes.

FIG. 1: Schematic representation a continuous flow reactor for the carbonylation of optionally functionalized alkenes using a CSTR reactor. The reactor is loaded with an optionally functionalized alkene; a catalyst system comprising a source of Pd and a ligand, a source of anions derived from an acid with a pKa<3, CO, and a hydroxylgroup comprising compound. Part of the carbonylation product is continuously removed via e.g. distillation, whereas CO, the hydroxylgroup comprising compound and residual alkene are fed back to the reactor. The other part of the alkene carbonylation product, containing catalyst, is fed back to the reactor.

Batch reactions were performed in a 160 mL Hastalloy C Parr autoclave. Dry methanol was purchased from Sigma Aldrich. Ligand α,α'-bis(di-tert-butylphosphino)xylene was purchased from Strem. Pd(OAc)$_2$ was purchased from Sigma Aldrich. All commercial chemicals were used as received. Methylpentenoates (mixture of all isomers) was prepared in house. Catalyst solutions were prepared in a nitrogen filled glovebox. In order to avoid mass transfer limitations, a gas-impelling stirrer was used.

EXAMPLE 1

DMA Stabilisation in Batch Process

An autoclave under nitrogen atmosphere was loaded with a solution of Pd(OAc)$_2$ (9 mg, 0.04 mmol), α,α'-bis(di-tert-butylphosphino)xylene (80 mg, 0.2 mmol), methanesulfonic acid (38 mg, 0.4 mmol), methylpentenoates (MP, mixture of all isomers), methanol and optionally dimethyladipate (DMA). Quantities are indicated in the table below. The autoclave was heated to 100° C. and pressurized to 20 bar of CO. The results are summarized in the table below. The turnover frequencies (TOF) were measured at 20% conversion (mol MP/mol Pd/h). In case no dimethyl adipate is added at the start of the reaction, Pd black is observed when the reaction is finished, indicating catalyst degradation. Moreover, addition of DMA as a stabilizer has hardly any effect on the catalyst activity. Results see Table 1.

TABLE 1

| Entry | MeOH (mL) | MP (mL) | DMA (mL) | DMA/Pd ratio | TOF | Observations |
|---|---|---|---|---|---|---|
| 1 | 40 | 20 | 0 | 0 | 1000 | Pd black |
| 2 | 30 | 15 | 15 | 1750 | 1280 | No Pd Black |
| 3 | 30 | 15 | 7.5 | 900 | 1235 | No Pd Black |
| 4 | 30 | 15 | 3.75 | 500 | 1200 | No Pd Black |
| 5 | 30 | 15 | 15 | 900 | 1200 | No Pd Black |

In experiment 5, a double amount of catalyst was used.

EXAMPLE 2

Catalyst Recycling: Repetitive Batch

An autoclave under nitrogen atmosphere is loaded with a solution of Pd(OAc)$_2$ (9 mg, 0.04 mmol), α,α'-bis(di-tert-butylphosphino)xylene (80 mg, 0.2 mmol), methanesulfonic acid (38 mg, 0.4 mmol), methylpentenoates (MP, mixture of all isomers), methanol and optionally dimethyladipate ("DMA initial").

The autoclave is heated to 100° C. and pressurized to 20 bar of CO. When the desired conversion is reached, the reactor is allowed to cool down to r.t. and CO is vented. Methanol, residual MP and the majority of the formed DMA (typically 60-80%) are distilled off (MP and DMA under reduced pressure). Then, a fresh solution of MP in methanol is added to the remaining catalyst solution in DMA (i.e. in the presence of DMA. The autoclave is again heated to 100° C. and pressurized to 20 bar of CO. This sequence is repeated several times. Results are shown in Table 2: if DMA is present neither initially or in subsequent reaction steps, Pd black is formed (+). If DMA is not present initially (i.e. is not added to the reaction mixture), and is present in the subsequent reaction steps, some Pd black is formed (+/−). However, if DMA is added initially, and is also present in the subsequent steps, no PD black is formed (−).

TABLE 2

| DMA initial | DMA next step | Pd black |
|---|---|---|
| − | − | + |
| − | + | +/− |
| + | + | − |

EXAMPLE 3

Catalyst Recycling: Continuous Flow

A CSTR reactor under nitrogen atmosphere is loaded with a solution of Pd(OAc)$_2$, α,α'-bis(di-tert-butylphosphino)xylene, methanesulfonic acid, methylpentenoates (MP, mixture of all isomers), methanol and optionally dimethyladipate (DMA). The reactor is heated to 100° C. and pressurized to 20 bar of CO. Part of the carbonylation product dimethyl adipate (DMA) is continuously removed via e.g. distillation, whereas CO, MeOH and residual MP are fed back to the reactor. The other part of DMA containing the catalyst is fed back to the reactor. When no DMA is added to the reactor, Pd black is formed. When DMA is added to the reactor, the amount of PD black has reduced.

EXAMPLE 4

Stabilisation by Methyl Nonanoate

An autoclave under nitrogen atmosphere is loaded with a solution of Pd(OAc)$_2$ (9 mg, 0.04 mmol), α,α'-bis(di-tert-butylphosphino)xylene (80 mg, 0.2 mmol), methanesulfonic acid (38 mg, 0.4 mmol), octene, methanol and optionally methyl nonanoate. The autoclave is heated to 100° C. and pressurized to 20 bar of CO.

When no methyl nonanoate is added at the start of the reaction, Pd black is observed when the reaction is finished, indicating catalyst degradation. When methyl nonanoate is added to the reactor, the amount of PD black has reduced. Moreover, addition of methyl nonanoate as a stabilizer has hardly any effect on the catalyst activity.

EXAMPLE 5

Stabilisation by Dimethyl Succinate

An autoclave under nitrogen atmosphere is loaded with a solution of Pd(OAc)$_2$ (9 mg, 0.04 mmol), α,α'-bis(di-tert-butylphosphino)xylene (80 mg, 0.2 mmol), methanesulfonic acid (38 mg, 0.4 mmol), methyl acrylate, methanol and optionally dimethyl succinate. The autoclave is heated and pressurized to 20 bar of CO. When no dimethyl succinate is added at the start of the reaction, Pd black is observed when the reaction is finished, indicating catalyst degradation. When dimethyl succinate is added to the reactor, the amount of Pd black has reduced. Moreover, addition of methyl nonanoate as a stabilizer has hardly any effect on the catalyst activity.

The invention claimed is:

1. A process for alkoxycarbonylation of carboxylic acid functionalized alkenes and/or esters thereof, said process comprising: (a) reacting (i) a carboxylic acid functionalized alkene and/or ester thereof; (ii) a catalyst system comprising a source of Pd and a ligand, (iii) an acid with a pKa<3, (iv) carbon monoxide, and (v) a hydroxyl group comprising compound, under conditions wherein an ester carbonylation product is produced, whereby the process is carried out in initial presence of the ester carbonylation product.

2. Process according to claim 1 comprising adding an ester carbonylation product.

3. Process according to claim 2 wherein the ester carbonylation product is added prior to adding the catalyst system and/or together with the catalyst system.

4. Process according to claim 1 wherein the ligand is a bidentate diphosphine ligand of formula II:

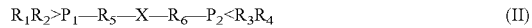

wherein P1 and P2 represent phosphorus atoms; $R_1$, $R_2$, $R_3$ and $R_4$ can independently represent the same or different optionally substituted organic group containing a tertiary carbon atom through which the group is linked to phosphorus atom; $R_5$ and $R_6$ independently represent optionally substituted lower alkylene groups; and X represents an optionally substituted aromatic group.

5. Process according to claim 4 wherein $R_5$ and $R_6$ represent methylene and wherein $R_1$, $R_2$, $R_3$, and $R_4$ represent tert-butyl.

6. Process according to claim 1 wherein the ligand is α-α'-bis(di-tert-butylphosphino)xylene.

7. Process according to claim 1 wherein the process is a continuous process.

8. Process according to claim 1 wherein the process is repetitive batch process, wherein said repetitive batch process further comprises
    (b) recovering the catalyst system from the ester carbonylation product in the presence of the ester carbonylation product; and
    (c) repeating (a) wherein at least part of the catalyst system in (a) is the recovered catalyst system obtained in (b).

9. Process according to claim 8 wherein at least 10% (w/w) of the catalyst system in (a) is the recovered catalyst system obtained in (b).

10. Process according to claim 1 wherein the carboxylic functionalized alkene is a pentenoate ester, optionally pentenoate methylester.

11. Process according to claim 1 wherein the source of Pd is at least one selected from the group consisting of a palladium halide, palladium carboxylate and Pd2(dba)3.

12. An ester carbonylation product capable of being used in the process of claim 1.

* * * * *